(12) United States Patent
Reddy

(10) Patent No.: US 8,099,175 B2
(45) Date of Patent: Jan. 17, 2012

(54) MEDICAL ELECTRICAL LEAD WITH PROXIMAL ARMORING

(75) Inventor: G. Shantanu Reddy, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 455 days.

(21) Appl. No.: 12/371,264

(22) Filed: Feb. 13, 2009

(65) Prior Publication Data

US 2009/0210043 A1   Aug. 20, 2009

Related U.S. Application Data

(60) Provisional application No. 61/028,999, filed on Feb. 15, 2008.

(51) Int. Cl.
*A61N 1/00* (2006.01)

(52) U.S. Cl. .......................................... 607/122

(58) Field of Classification Search ............ 607/122
See application file for complete search history.

(56) References Cited

U.S. PATENT DOCUMENTS

| | | | |
|---|---|---|---|
| 5,231,996 A | 8/1993 | Bardy et al. | |
| 5,246,014 A | 9/1993 | Williams et al. | |
| 5,358,516 A | 10/1994 | Myers et al. | |
| 5,674,272 A | 10/1997 | Bush et al. | |
| 5,845,396 A | 12/1998 | Altman et al. | |
| 5,917,346 A | 6/1999 | Gord | |
| 5,931,862 A | 8/1999 | Carson | |
| 6,705,900 B2 * | 3/2004 | Sommer et al. | 439/668 |
| 6,717,056 B2 | 4/2004 | Rivelli et al. | |
| 7,238,883 B2 | 7/2007 | Zarembo | |
| 7,292,894 B2 | 11/2007 | Belden | |
| 7,366,573 B2 | 4/2008 | Knapp et al. | |
| 7,519,432 B2 | 4/2009 | Bolea et al. | |
| 7,551,967 B1 | 6/2009 | Karicherla et al. | |
| 7,946,980 B2 | 5/2011 | Reddy et al. | |
| 2009/0319012 A1 | 12/2009 | Garabedian et al. | |

FOREIGN PATENT DOCUMENTS

| | | |
|---|---|---|
| EP | 1 844 812 A1 | 10/2007 |
| WO | WO 02/087689 | 11/2002 |
| WO | WO 02/089909 | 11/2002 |

OTHER PUBLICATIONS

International Search Report and Written Opinion issued in PCT/US2009/034083, mailed May 11, 2009, 14 pages.
International Search Report and Written Opinion issued in PCT/US2009/034086, mailed May 18, 2009, 13 pages.
Gallik, Donna M. et al., "Lead Fracture in Cephalic Versus Subclavian Approach with Transvenous Implantable Cardioverter Defibrillator Systems" PACE, vol. 19, Jul. 1996, pp. 1089-1094.

(Continued)

*Primary Examiner* — George Manuel
(74) *Attorney, Agent, or Firm* — Faegre & Benson LLP

(57) ABSTRACT

A medical electrical lead includes a flexible, insulative body defining a proximal region, an intermediate region, and a distal region. The proximal region is configured to be implanted at a subcutaneous implantation site, and is dimensioned to extend from an implantation location of the pulse generator to a location distal to a cardiovascular system entry site. The intermediate region is configured to extend distally from the proximal region to a location distal to a superior vena cava of a patient's heart, and the distal region is configured to extend distally from the intermediate region within the patient's heart. The lead further includes an armoring layer disposed on the lead body covering at least the proximal region.

18 Claims, 7 Drawing Sheets

OTHER PUBLICATIONS

Magney, Jean E. et al., "Pacemaker and Defibrillator Lead Entrapment: Case Studies", PACE, vol. 18, Aug. 1995, pp. 1509-1517.

Magney, Jean E. et al., "Anatomical Mechanisms Explaining Damage to Pacemaker Leads, Defibrillator Leads, and Failure of Central Venous Catheters Adjacent to the Sternoclavicular Joint", PACE, vol. 16, Mar. 1993, Part 1, pp. 445-457.

Magney, Jean E. et al., "A New Approach to Percutaneous Subclavian Venipuncture to Avoid Lead Fracture or Central Venous Catheter Occlusion", PACE, vol. 16, Nov. 1993, pp. 2133-2142.

Roelke, Marc et al., "Subclavian Crush Syndrome Complicating Transvenous Cardioverter Defibrillator Systems", PACE, vol. 18, May 1995, Part 1, pp. 973-979.

* cited by examiner

MEDICAL ELECTRICAL LEAD WITH PROXIMAL ARMORING

CROSS-REFERENCE TO RELATED APPLICATION

This application claims priority to U.S. Provisional Application No. 61/028,999, filed Feb. 15, 2008, which is incorporated herein by reference in its entirety.

TECHNICAL FIELD

The present invention relates to medical electrical leads for use in cardiac rhythm management systems, and in particular, to medical electrical leads configured for partial implantation in a heart of a patient.

BACKGROUND

Various types of medical electrical leads for use in cardiac rhythm management systems are known. Such leads typically extend intravascularly to an implantation location within or on a patient's heart, and thereafter coupled to a pulse generator or other implantable device for sensing cardiac electrical activity, delivering therapeutic stimuli, and the like. The leads are desirably highly flexible to accommodate natural patient movement, yet also constructed to have minimized profiles. At the same time, the leads are exposed to various external forces imposed, for example, by the human muscular and skeletal system, the pulse generator, other leads, and surgical instruments used during implantation and explantation procedures. There is a continuing need for improved lead designs.

SUMMARY

The present invention, in one embodiment, is a medical electrical lead configured to be coupled to a pulse generator in a cardiac rhythm management system. The lead comprises a proximal connector, a flexible body, an armoring layer, at least one electrode, and at least one electrical conductor. The proximal connector is configured to mechanically and electrically couple the lead to the pulse generator. The flexible body extends distally from the connector and defines a proximal region, an intermediate region, and a distal region terminating in a distal tip. The armoring layer is disposed over the proximal region of the lead body and not over the distal region of the lead body, and includes a polymeric material having a lubricious outer surface configured to resist abrasion, and a reinforcing material disposed within the armoring layer. The electrode is coupled to the lead body in the distal region, and the electrical conductor extends from the electrode to the connector for electrically coupling the at least one electrode thereto.

In another embodiment, the present invention is a medical electrical lead configured to be coupled to a pulse generator in a cardiac rhythm management system. The lead comprises a proximal connector configured to mechanically and electrically couple the lead to the pulse generator, a flexible body extending distally from the connector, at least one electrode, and at least one electrical conductor. The flexible body defines a proximal region, an intermediate region, and a distal region terminating in a distal tip. The electrode is coupled to the lead body in the distal region, and the conductor extends from the electrode to the connector for electrically coupling the at least one electrode thereto. The lead further comprises armoring means for reinforcing and increasing abrasion resistance of at least the proximal region. The armoring means is disposed over the proximal region of the lead body but not the distal region of the lead body.

In yet another embodiment, the present invention is a medical electrical lead configured to be coupled to a pulse generator in a cardiac rhythm management system. The lead comprises a proximal connector, a flexible body, an armoring layer, at least one electrode, and at least one electrical conductor. The connector is configured to mechanically and electrically couple the lead to the pulse generator. The body extends distally from the connector and defines a proximal region, an intermediate region, and a distal region. The proximal region is configured to be implanted substantially subcutaneously, and is dimensioned to extend from an implantation location of the pulse generator to a location distal to a cardiovascular system entry site. The intermediate region is configured to extend distally from the proximal region to a location distal to a superior vena cava of a patient's heart. The distal region terminates in a distal tip, and is configured to extend distally from the intermediate region within the patient's heart. The armoring layer is disposed over only the proximal and intermediate regions of the lead body. The armoring layer includes a lubricious polymeric material and extends distally from the connector and terminates proximal to the intermediate region of the lead body. The electrode is coupled to the lead body in the distal region, and the electrical conductor extends from the electrode to the connector for electrically coupling the at least one electrode thereto.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
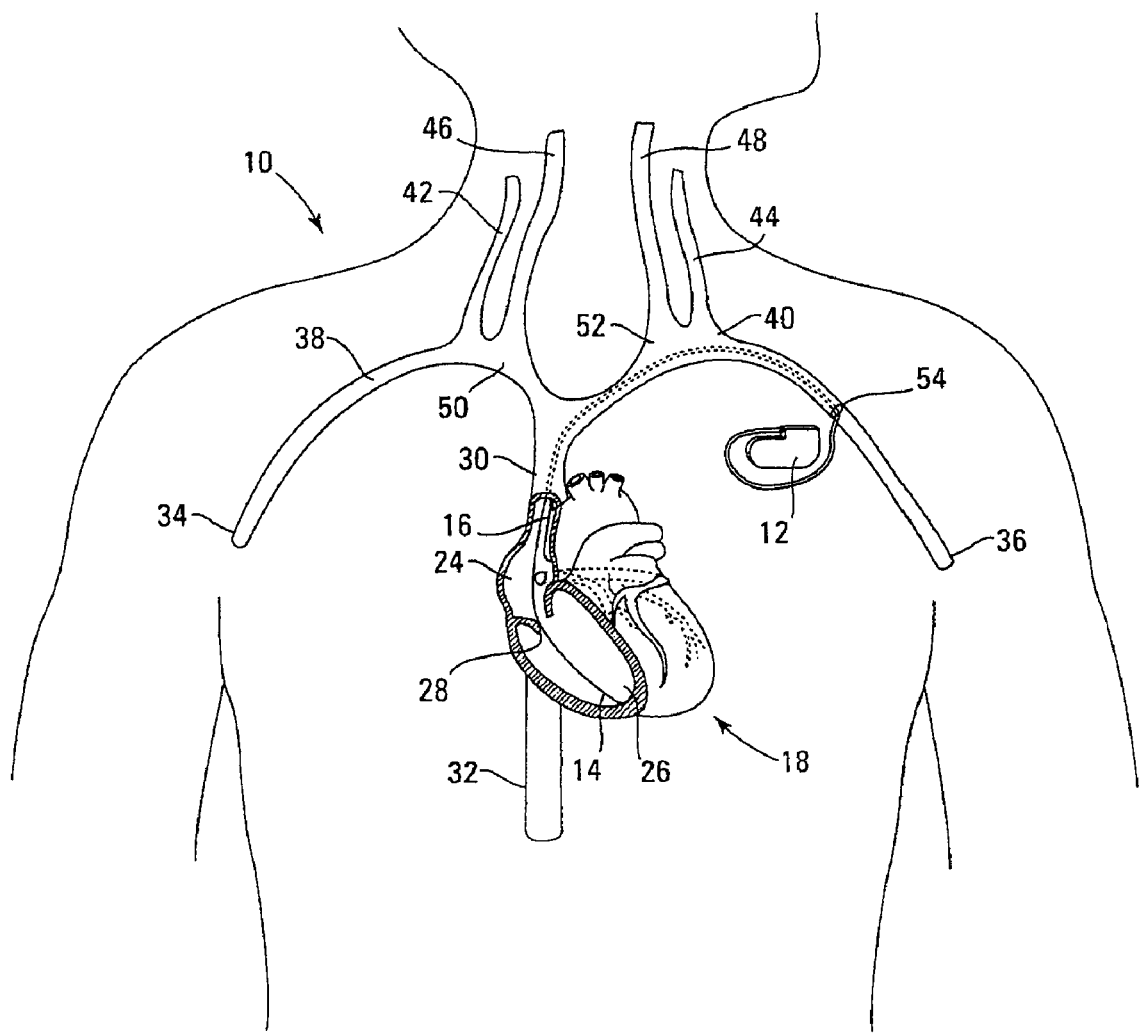
FIG. 1 is a schematic view of a cardiac rhythm management (CRM) system including a pulse generator and a lead implanted in a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments of the present invention, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, and/or includes both pacing and defibrillation capabilities. The portion of the leads 14, 16 extending from the pulse generator 12 to the vascular entry site 54 are also located subcutaneously or submuscularly. Any excess lead length, i.e., length beyond that needed to reach from the pulse generator 12 location to the desired intracardiac implantation site, is generally coiled up in the subcutaneous pocket near the pulse generator 12.

Figure 2:
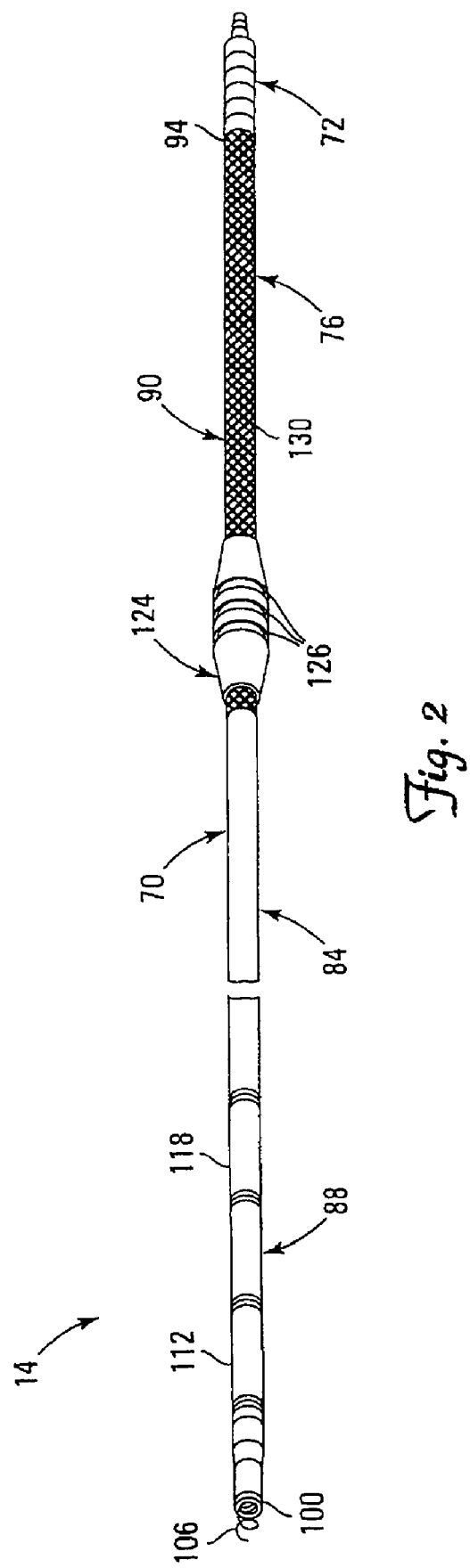
FIG. 2 is an isometric illustration of the lead of FIG. 1.

FIG. 2 is an isometric illustration of the lead 14. As shown in FIG. 2, the lead 14 includes, in one embodiment, an elongated body 70 and a proximal connector 72 coupled thereto. As further shown, the lead body 70 defines a proximal region 76, an intermediate region 84, and a distal region 88. The lead 14 further includes an armoring layer 90 on the lead body 70 in the proximal region 76. The proximal region 76 is dimensioned to extend from the implanted pulse generator 12 and into the vascular system, e.g., into the left subclavian vein 40 (see FIG. 1), just distal to the vascular entry site 54. Thus, the proximal region 76 is located generally subcutaneously when the lead 14 is implanted, with a marginal length extending intravascularly.

The intermediate region 84 is dimensioned to extend intravascularly from the proximal region 76, i.e., from just distal to the vascular entry site 54, through the left subclavian vein 40 and the left brachiocephalic vein 52 and into the superior vena cava 30. Finally, the distal region 88 is configured as an intracardiac region, and thus to extend into the right atrium 24, through the tricuspid valve 28, and into the right ventricle 26 where the distal tip 100 is implanted. In the illustrated embodiment, the intermediate and distal regions 84, 88 are substantially isodiametric, and are configured to have sufficient flexibility to accommodate natural motion of the heart 12. In various embodiments, these regions are also configured to impede or substantially prevent tissue ingrowth.

The proximal region 76 has a proximal end 94 coupled to the connector 72, and the distal region 88 terminates at a distal tip 100. The connector 72 is configured to mechanically and electrically couple the lead 14 to a header on the pulse generator 12. The lead 14 also includes a fixation helix 106 and a pair of coil electrodes 112, 118. In the illustrated embodiment, the electrodes 112, 118 are shocking electrodes for providing a defibrillation shock to the heart 18, and each includes a coating configured to control (i.e., promote or discourage) tissue in-growth. In one embodiment, the electrodes are coated with an expanded polytetrafluoroethylene (ePTFE) coating configured to permit intimate fluid contact between the electrodes 112, 118 and the cardiac tissue, and also to substantially prevent tissue ingrowth and fibrosis that could otherwise adhere to the electrode surfaces. Additionally, the fixation helix 106 may also be configured as a pace/sense electrode. In various other embodiments, other electrode configurations may be employed depending on the particular therapeutic needs of the patient.

As further shown in FIG. 2, the lead 14 further includes a suture sleeve 124 disposed about the lead body 70 in the proximal region 76. The suture sleeve 124 includes a plurality of circumferential grooves 126, and facilitates securing the proximal region 76 in its desired implantation. For example, sutures (not shown) can be located partially within the grooves and through surrounding or adjacent facial tissue, and pulled tight and secured to inhibit or substantially prevent spontaneous longitudinal movement of the lead 14. Tightening the sutures results in a compressive force being applied to the lead body 70 by each suture, and the suture sleeve 124 operates in part to distribute these compressive forces along the lead body 70 to avoid damage thereto.

The lead body 70 can be made from any flexible, biocompatible materials suitable for lead construction. In various embodiments, the lead body 70 is made from a flexible, electrically insulative material. In one embodiment, the lead body is made from silicone rubber. In another embodiment, the lead body is made from polyurethane. In various embodiments, the proximal, intermediate and distal regions 76, 84, and 88, respectively, are made from different materials selected to provide desired functionalities.

The armoring layer 90 extends about the proximal region 76 from the connector 72 to the intermediate region 84. The armoring layer 90 operates, in part, to enhance the overall strength and/or durability of proximal region 76. For example, in one embodiment, the armoring layer 90 is configured to enhance the abrasion resistance of the proximal region 76, which can be subject to abrasion due to the interaction of the lead 14 with other structures and/or devices, e.g., the lead 16 and/or the pulse generator 12 shown in FIG. 1.

In one embodiment, the armoring layer 90 is configured to enhance resistance to damage due to high temperatures which may be caused, for example, by electrocautery equipment used to dissect other leads and/or the pulse generator 12 away from fibrosed tissue in order to replace and/or repair such devices. In various embodiments, the armoring layer 90 is configured to enhance the crush resistance of the proximal region 76. The latter functionality is advantageous, for example, in the portion of the proximal region 76 covered by and near the suture sleeve 124. In one embodiment, the armoring layer 90 is configured to enhance the resistance of the proximal region 76 to physical damage, e.g., cuts, caused by surgical instruments such as scalpels and the like. Of course in various embodiments, the armoring layer 90 is configured to exhibit combinations of the above-mentioned properties. In still other embodiments, the armoring layer 90 is configured to provide other functionality aimed at enhancing the resistance of the proximal region 76 to damage during operation and medical procedures.

In the illustrated embodiment, the armoring layer 90 is a covering of polymeric material disposed over the lead body 70. The specific polymer materials selected are based on the desired armoring functionality. In various embodiments, the armoring layer 90 is made completely or substantially from polymeric materials including ePTFE, polytetrafluoroethylene (PTFE), polyethylene, silicone rubber, polyurethane, and polymers of the above. In one embodiment, the armoring layer 90 is made substantially from a polyurethane-based polymer. In one embodiment, the armoring layer 90 is made from a silicone-polyurethane co-polymer. In various embodiments, the armoring layer 90 is made of a lubricious material such as ePTFE and/or PTFE, which provides enhanced abrasion resistance as well as resistance to high temperature/ electrocautery damage and also inhibit tissue ingrowth and fibrosis. Still other materials can be employed to provide specific desired characteristics.

In various embodiments, the armoring layer 90 includes two or more layers of polymeric materials each specified for a desired functionality. For example, in one embodiment, the armoring layer 90 includes a layer of silicone rubber, which provides resistance to damage caused by high temperature and/or electrocautery equipment, over a layer of polyurethane, which provide good abrasion resistance. In various other embodiments, other combinations of polymer layers may be employed.

The armoring layer 90 can be formed by any suitable process. In one embodiment, the armoring layer 90 is in the form of a tape or ribbon wrapped about the lead body 70. In one embodiment, the armoring layer 90 is an ePTFE tape or ribbon wrapped about the lead body 70. Alternatively, the armoring layer 90 can be, in various embodiments, a polymer extrusion, e.g., an ePTFE or PTFE extrusion. The armoring layer 90 can also be in the form of a separate tubular member inserted over and adhered to the lead body 70. In still other embodiments, the polymer armoring layer 90 is deposited by spray, vapor deposition, dipping, and other coating process. In short, the specific construction and manufacturing process utilized to form the armoring layer 90 is not limited.

In various embodiments, as shown and discussed in greater detail below, the armoring layer 90 includes reinforcing materials (e.g., wire or braid) in addition to the polymeric layer described above. Such reinforcing materials operate to improve the crush resistance and overall strength of the proximal region 76.

Figure 3A:
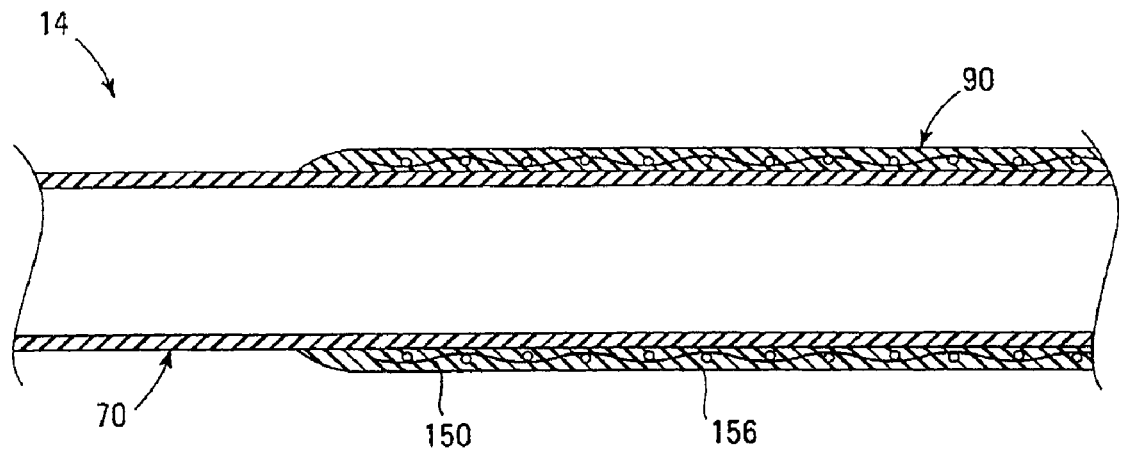
FIGS. 3A-3C are partial cross-sectional views of the lead of FIG. 1.

FIG. 3A is a partial cross-sectional schematic view of the lead 14 according to one embodiment of the present invention. For illustration purposes only, internal features of the lead 14, e.g., cable and coil conductors, are omitted from the illustration of FIG. 3A. In the embodiment illustrated in FIG. 3A, the armoring layer 90 includes a reinforcing fiber braid 150 embedded within a polymer layer 156. The configuration of the braid 150 can be selected so as to provide a desired degree of flexibility and strength for enhancing crush resistance, cut resistance, compressive and tensile strength, and the like. In various embodiments, the braid 150 is positioned over the lead body 70, e.g., in a sheet or tubular form, and the polymer layer 156 is coated onto the lead body 70 over the braid 150, such that the braid 150 becomes embedded within the polymer layer 156. Alternatively, in other embodiments, the armoring layer 90 is formed as a separate structure including the braid 150 and the polymer layer 156, and then slipped over and adhered to the lead body 70 by any suitable process, e.g., medical adhesive, shrink-wrapping, etc. In other embodiments, the polymer layer 156 may be a tape or ribbon, e.g., of ePTFE or PTFE, that is itself reinforced with the braid 150. In still other embodiments, other configurations may be employed.

Figure 3B:
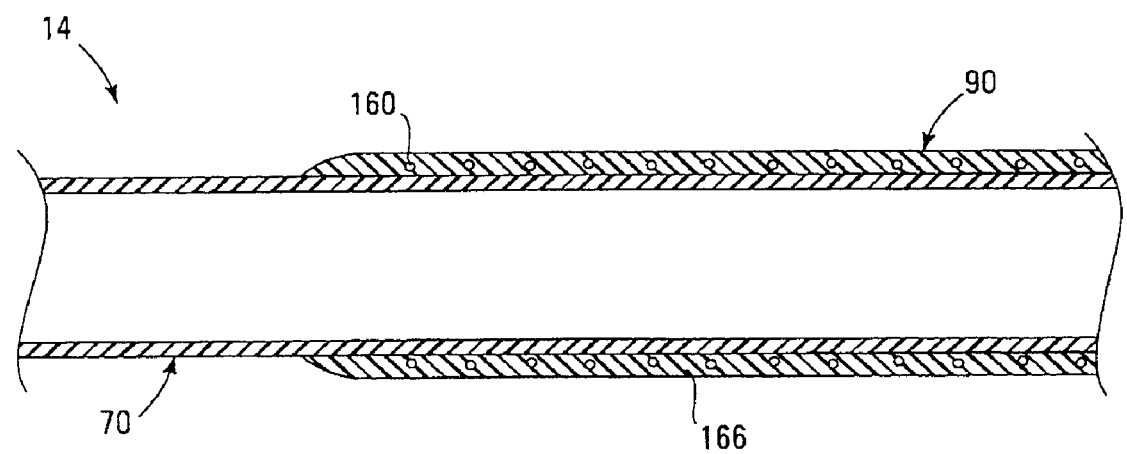

FIG. 3B is a partial cross-sectional schematic view of the lead 14 according to another embodiment of the present invention. For illustration purposes only, internal features of the lead 14, e.g., cable and coil conductors, are omitted from the illustration of FIG. 3B. In the embodiment illustrated in FIG. 3B, the armoring layer 90 includes a reinforcing wire 160 wound about the lead body 70 and embedded within a polymer layer 166. In the illustrated embodiment, the wire 160 has a generally circular cross-sectional shape, although in other embodiments, other wire shapes, e.g., flat, are used. Similarly to the embodiment of FIG. 3A, the configuration of the wire 160 is selected so as to provide a desired degree of flexibility and strength for enhancing crush resistance, cut resistance, compressive and tensile strength, and the like. In various embodiments, the wire 160 is wound about the lead body 70 and the polymer layer 166 is coated onto the lead body 70 over the wire 160, such that the wire 160 becomes embedded within the polymer layer 166. Alternatively, in other embodiments, the armoring layer 90 is formed as a separate structure including the wire 160 and the polymer layer 166, and then slipped over and adhered to the lead body 70. In other embodiments, the polymer layer 166 may be a tape or ribbon, e.g., of ePTFE or PTFE, that is itself reinforced with the wire 160.

In the embodiments of FIGS. 3A and 3B, the braid 150 and/or the wire 160 can be made from any materials providing the desired degree of strength, e.g., for crush and cut resistance, and flexibility. In various embodiments, polymeric and metallic wires and fibers are used. In various embodiments, the braid 150 or the wire 160 may be made from a superelastic metal or polymer. Exemplary metallic braid and wire materials include, without limitation, stainless steel, MP35N, nickel titanium alloys, e.g., nitinol, and the like.

Figure 3C:
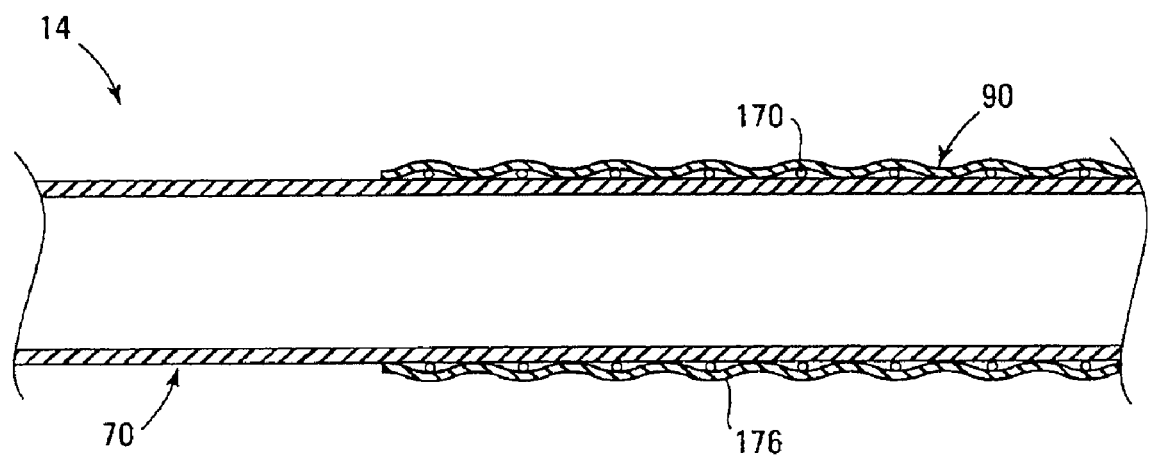

FIG. 3C is a partial cross-sectional schematic view of yet another embodiment of the lead 14. For illustration purposes only, internal features of the lead 14, e.g., cable and coil conductors, are omitted from the illustration of FIG. 3C. In the embodiment of FIG. 3C, the armoring layer 90 includes a wire 170 wound about the lead body 70 and covered with a polymer layer 176. This embodiment differs from that of FIG. 3B in that the wire 170 is not embedded within the polymer layer 176. Rather, the polymer layer 176 provides a covering layer over the wire 170. In various embodiments, the polymer layer 176 may be a tape or ribbon wrapped over the wire 170, a tubular structure slid over the wire 170, or may be applied as a coating over the wire 170. In various embodiments, a braid or weave, such as the braid 150 of FIG. 3A, can be used to reinforce the armoring layer 90 in the same manner as the wire 170.

Of course in various embodiments, the armoring layer 90 is formed only of one or more polymer layers, and does not include a reinforcing braid, wire, or the like.

Figure 4:
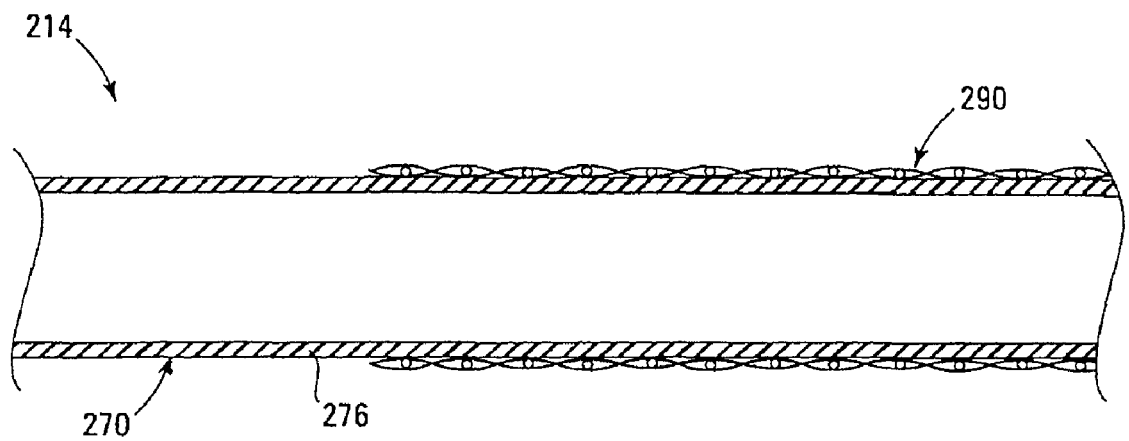
FIG. 4 is a partial cross-sectional view of an alternative lead for use in the CRM system of FIG. 1, according to another embodiment of the present invention.

FIG. 4 is a partial cross-sectional schematic view of an alternative lead 214 according to another embodiment of the present invention. For illustration purposes only, internal features of the lead 214, e.g., cable and coil conductors, are omitted from the illustration of FIG. 4. The lead 214 is in most respects similar to the lead 14, and includes a flexible, insulative lead body 270 defining, in part, a proximal region 276, and an armoring layer 290 disposed over the lead body 270. In the illustrated embodiment, the armoring layer 290 is in the form of a weave or braid without a polymeric layer such as in the embodiments described above. In one embodiment, the armoring layer 290 is a synthetic fiber braid, such as that sold under the brand name Kevlar®. In other embodiments, the armoring layer 290 may be a polymeric or metallic weave, braid, or coil.

Figure 5:
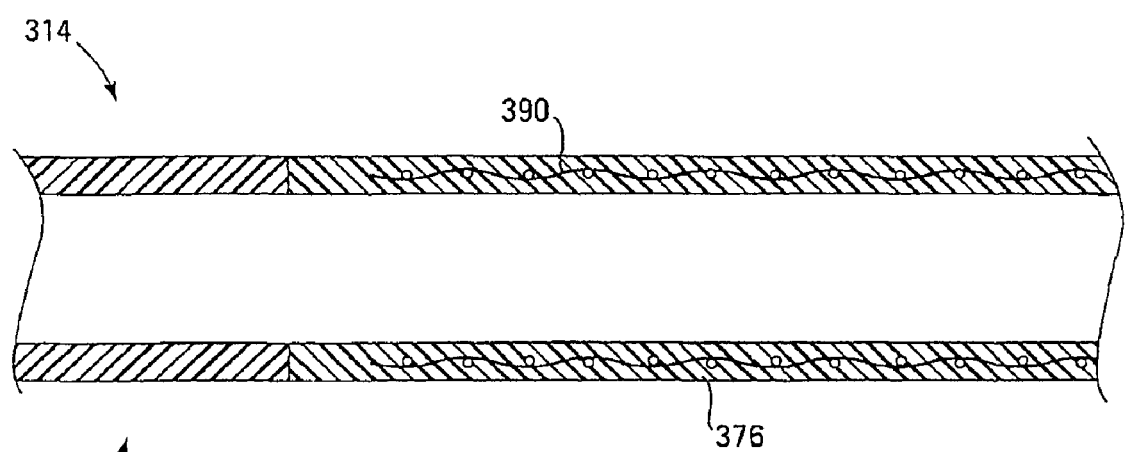
FIG. 5 is a partial cross-sectional view of an alternative lead for use in the CRM system of FIG. 1, according to another embodiment of the present invention.

FIG. 5 is a partial cross-sectional schematic view of an alternative lead 314 according to another embodiment of the present invention. For illustration purposes only, internal features of the lead 314, e.g., cable and coil conductors, are omitted from the illustration of FIG. 5. The lead 314 is in most respects similar to the lead 14, and includes a flexible, insulative lead body 370 defining, in part, a proximal region 376. In the illustrated embodiment, lead body 370 in the proximal region 376 also operates as an armoring layer, and includes an armoring element 390 integrally formed into the lead body 370. The armoring element 390 can include any of the weaves, braids, wires, coils, and the like described above. Thus, in the embodiment of FIG. 5, the lead body 370 is armored in at least the proximal region 376 even though it does not include a separate armoring layer disposed over the outer surface of the lead body 370. This embodiment advantageously allows the armored proximal region 376 and any unarmored regions of the lead 314 to be substantially or entirely isodiametric.

Figure 6:
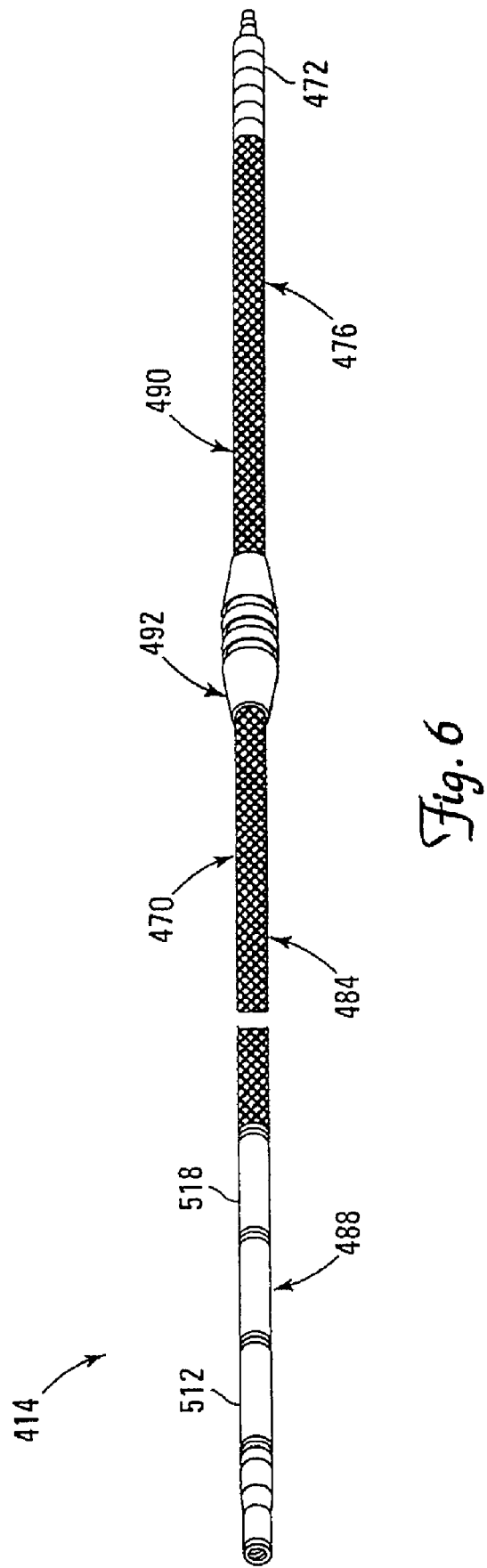
FIG. 6 is an isometric illustration of an alternative lead for use in the CRM system of FIG. 1, according to another embodiment of the present invention.

FIG. 6 is an isometric illustration of a lead 414 according to another embodiment of the present invention. The lead 414 is in most respects similar or identical to the leads 14, 214, and 314 shown and described above, and includes an elongated body 470 and a proximal connector 472 coupled thereto. As further shown, the lead body 470 defines a proximal region 476, an intermediate region 484, and a distal region 488. The lead 414 further includes an armoring layer 490 on the lead body 470. As with the other lead embodiments described above, the proximal region 476 is dimensioned to extend from the implanted pulse generator 12 and into the vascular system, e.g., into the left subclavian vein 40 (see FIG. 1), the intermediate region 484 is dimensioned to extend intravascularly from the proximal region 476, and the distal region 388 is configured as an intracardiac region of the lead 414 so as to extend within the heart. As illustrated, the lead 414 further includes a suture sleeve 492 similar or identical to the suture sleeve 124 of the lead 14.

In the embodiment of FIG. 6, the armoring layer 490 extends from the connector 472 to the proximal end of the distal region 488. Thus, both the proximal region 476 and the intermediate region 484 of the lead 414 are covered by the armoring layer 490. The illustrated configuration ensures that the portion of the lead body 470 covered by the suture sleeve 492 and adjacent the vascular entry site 54 (see FIG. 1) is armored. In various such embodiments, the armoring layer 490 extends from the connector 472 to a location approximately 25 centimeters proximal to the distal tip of the lead 414.

The lead 414 in general and the armoring layer 490 in particular, can be configured in the same manner as any of the embodiments described above. In the illustrated embodiment, the lead 414 includes a fixation helix 506 and a plurality of coil electrodes 512, 518. In the illustrated embodiment, the electrodes 512, 518 are shocking electrodes for providing a defibrillation shock to the heart, and each include a coating configured to control (i.e., promote or discourage) tissue ingrowth. In one embodiment, the electrodes are wrapped with an ePTFE tape coating. In one such embodiment, the armoring layer 490 is formed at least partially by extending the ePTFE tape wrap proximally from the proximal electrode 418 toward the proximal connector 472. Alternatively, the ePTFE tape armoring layer 390 is a separate structure that is joined to the ePTFE covering over the electrode 518. Of course, in other embodiments, other armoring layer configurations described above can be employed.

Each of the lead embodiments of FIGS. 2-6 include electrodes configured for delivering defibrillation stimuli. In other embodiments, other types of implantable medical electrical leads include one or more armored regions such as those described above. For example, the armored lead concepts described above may also be incorporated into leads configured for pacing one or more of the right atrium, the right ventricle, or the left ventricle (see FIG. 1).

Figure 7:
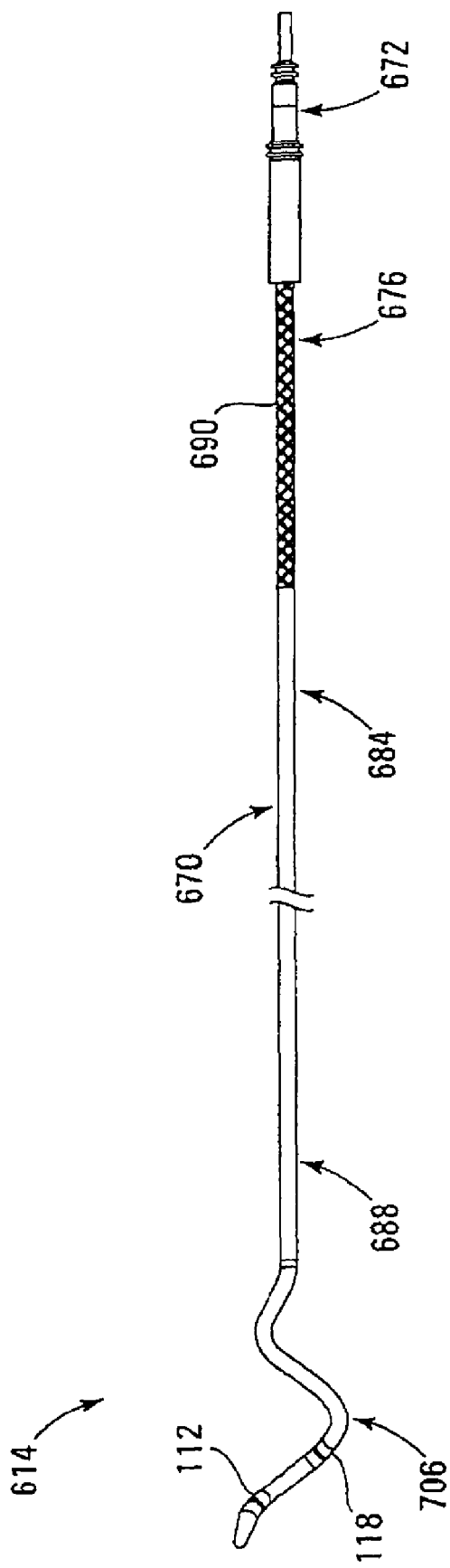
FIG. 7 is an isometric illustration of an alternative lead for use in a CRM system according to another embodiment of the present invention.

For example, FIG. 7 illustrates an alternative embodiment of a lead 614 suitable for pacing the left ventricle, e.g., in a bi-ventricular pacing or cardiac resynchronization therapy system. As is known, such leads are typically configured to extend intravascularly into the right atrium and the coronary sinus (the large vein draining blood from the coronary venous system into the right atrium), and ultimately into a coronary vein adjacent the left ventricular wall. Accordingly, as shown in FIG. 7, the lead 614 includes an elongated body 670 and a proximal connector 672 coupled thereto. As further shown, the lead body 670 defines a proximal region 676, an intermediate region 684, and a distal region 688. The lead 614 further includes an armoring layer 690 on the lead body 670 in the proximal region 676.

Similar to the other lead embodiments described above, the proximal region 676 is dimensioned to extend from the implanted pulse generator 12 and into the vascular system, e.g., into the left subclavian vein 40 (see FIG. 1), just distal to the vascular entry site 54. Thus, the proximal region 676 is located generally subcutaneously when the lead 14 is implanted, with a marginal length extending intravascularly. The intermediate region 684 is dimensioned to extend intravascularly from the proximal region 676, i.e., from just distal to the vascular entry site 54, through the left subclavian vein 40 and the left brachiocephalic vein 52 and into the superior vena cava 30. Finally, the distal region 688 is configured to extend into the right atrium 24, through the coronary sinus (not shown in FIG. 1) to a desired implantation sight in a coronary vein adjacent the left ventricle.

In the illustrated embodiment, the distal region 688 includes a pair of ring electrodes 712, 718 for sensing cardiac electrical activity and/or delivering an electrical stimulus to the cardiac tissue. In other embodiments, the lead 614 includes more or fewer electrodes. The distal region 688 of the lead 614 further includes a pre-formed helical shape to facilitate fixation of the distal region 688 within the coronary venous system. As will be appreciated, in other embodiments, additional or alternative fixation techniques may be employed—e.g., different pre-formed shapes, tines, expandable fixation elements such as stents, and the like.

Because the proximal region 676 is implanted generally subcutaneously, the operating and delivery requirements of this region are similar to those discussed above with respect to the other embodiments. Thus, the armoring layer 690 operates to enhance this regions' resistance to abrasion, crushing, cutting, high temperatures, and/or to otherwise enhance the strength and durability of the proximal region 676. As will be appreciated, the armoring layer 690 can take on any of the forms discussed above in connection with the leads 14, 214, 314, and 414. In the illustrated embodiment, only the proximal region 676 includes the armoring layer 690, so as to not affect the strength and flexibility of the intermediate and distal regions 684, 688. In other embodiments, one or both of the intermediate and distal regions 684, 688 (or portions thereof), include the armoring layer 690 in addition to or in lieu of the proximal region 676.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A medical electrical lead configured to be coupled to a pulse generator in a cardiac rhythm management system, the lead comprising:
    a proximal connector configured to mechanically and electrically couple the lead to the pulse generator;
    a flexible body extending distally from the connector, the body defining a proximal region, an intermediate region, and a distal region terminating in a distal tip;
    an armoring layer disposed over the proximal region of the lead body and not over the distal region of the lead body, the armoring layer including a polymeric material having a lubricious outer surface configured to resist abrasion, and a reinforcing material disposed within the armoring layer, wherein the proximal region is configured to be implanted substantially subcutaneously, and is dimensioned to extend from an implantation location of the pulse generator to a location distal to a cardiovascular entry site;
    at least one electrode coupled to the lead body in the distal region; and
    at least one electrical conductor extending from the at least one electrode to the connector for electrically coupling the at least one electrode thereto.

2. The lead of claim 1 wherein the polymeric material is ePTFE or PTFE.

3. The lead of claim 2 wherein the polymeric material is ePTFE tape wound circumferentially about the lead body.

4. The lead of claim 1 wherein the reinforcing material includes a flexible braid embedded within the polymeric material.

5. The lead of claim 1 wherein the reinforcing material includes a wire or ribbon configured as a helical coil embedded within the polymeric material of the armoring layer.

6. The lead of claim 1 wherein:
    the reinforcing material is a flexible braid disposed over the lead body; and
    the polymeric material is disposed over the braid.

7. The lead of claim 1 wherein:
    the reinforcing material is a wire or ribbon configured as a helical coil wound about the lead body; and
    the polymeric material is disposed over the coil.

8. The lead of claim 1 wherein:
    the intermediate region is configured to extend distally from the proximal region to a location distal to a superior vena cava of a patient's heart; and
    the distal region is configured to extend distally from the intermediate region within the patient's heart.

9. The lead of claim 8 wherein:
    the at least one electrode includes:
        a coil electrode coupled to the lead body in the distal region; and
        a tip electrode in the form of a fixation helix configured to penetrate cardiac tissue extending distally from the distal tip of the body; and
    the at least one electrical conductor includes:
        a first conductor extending from the cod electrode to the connector; and
        a second connector extending from the tip electrode to the connector.

10. The lead of claim 9 further comprising a layer of polymeric material disposed over at least a portion of the coil electrode for inhibiting tissue ingrowth thereto.

11. The lead of claim 10 wherein the layer of polymeric material disposed over at least a portion of the coil electrode is an ePTFE ribbon wrapped circumferentially about at least a portion of the coil electrode.

12. The lead of claim 11 wherein the armoring layer is further disposed over the intermediate region of the lead body.

13. The lead of claim 12 wherein the ePTFE ribbon extends proximally from the coil electrode to form the polymeric material of the armoring layer.

14. The lead of claim 13 wherein the reinforcing material is a flexible braid disposed between the lead body and the ePTFE ribbon in the intermediate and proximal regions of the lead.

15. The lead of claim 13 wherein the reinforcing material is a flexible wire or ribbon helically wrapped about the lead body between the lead body and the ePTFE ribbon in the intermediate and proximal regions of the lead.

16. A medical electrical lead configured to be coupled to a pulse generator in a cardiac rhythm management system, the lead comprising:
    a proximal connector configured to mechanically and electrically couple the lead to the pulse generator;
    a flexible body extending distally from the connector, the body defining a proximal region, an intermediate region, and a distal region terminating in a distal tip;
    at least one electrode coupled to the lead body in the distal region; and
    at least one electrical conductor extending from the at least one electrode to the connector for electrically coupling the at least one electrode thereto; and
    armoring means for reinforcing and increasing abrasion resistance of at least the proximal region, the armoring means extending over the proximal region of the lead body but not the distal region of the lead body, wherein the proximal region is configured to be implanted substantially subcutaneously, and is dimensioned to extend from an implantation location of the pulse generator to a location distal to a cardiovascular entry site.

17. The lead of claim 16 further comprising armoring means for reinforcing and increasing abrasion resistance of the intermediate region.

18. A medical electrical lead configured to be coupled to a pulse generator in a cardiac rhythm management system, the lead comprising:
    a proximal connector configured to mechanically and electrically couple the lead to the pulse generator;
    a flexible body extending distally from the connector, the body defining:
        a proximal region configured to be implanted substantially subcutaneously, and is dimensioned to extend from an implantation location of the pulse generator to a location distal to a cardiovascular entry site;
        an intermediate region configured to extend distally from the proximal region to a location distal to a superior vena cava of a patient's heart; and a distal region terminating in a distal tip, the distal region being configured to extend distally front the intermediate region within the patient's heart;

an armoring layer disposed over only the proximal and intermediate regions of the lead body, the armoring layer including a lubricious polymeric material and a reinforcing material embedded in the polymeric material, the armoring layer extending distally from the connector and terminating proximal to the intermediate region of the lead body;

at least one electrode coupled to the lead body in the distal region; and at least one electrical conductor extending from the at least one electrode to the connector for electrically coupling the at least one electrode thereto.

* * * * *